United States Patent
Umebayashi (10) Patent No.: US 9,132,041 B2
(45) Date of Patent: Sep. 15, 2015

(54) DISPOSABLE WORN ARTICLE IN PANTS FORM WITH CUT-OUTS AND METHOD FOR MANUFACTURING SAME

(75) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 346 days.

(21) Appl. No.: 13/696,353

(22) PCT Filed: Jun. 27, 2011

(86) PCT No.: PCT/JP2011/064666
§ 371 (c)(1),
(2), (4) Date: Nov. 6, 2012

(87) PCT Pub. No.: WO2012/011366
PCT Pub. Date: Jan. 26, 2012

(65) Prior Publication Data
US 2013/0053811 A1 Feb. 28, 2013

(30) Foreign Application Priority Data
Jul. 23, 2010 (JP) .................. 2010-165812

(51) Int. Cl.
| | |
|---|---|
| *A61F 13/49* | (2006.01) |
| *A61F 13/493* | (2006.01) |
| *A61F 13/496* | (2006.01) |
| *A61F 13/15* | (2006.01) |
| *A61F 13/56* | (2006.01) |

(52) U.S. Cl.
CPC ........... *A61F 13/15* (2013.01); *A61F 13/15756* (2013.01); *A61F 13/15804* (2013.01); *A61F 13/49* (2013.01); *A61F 13/496* (2013.01); *A61F 13/56* (2013.01); *A61F 13/565* (2013.01)

(58) Field of Classification Search
CPC .............. A61F 13/496; A61F 13/5622; A61F 13/5638; A61F 13/5655; A61F 13/58; A61F 13/62; A61F 13/622; A61F 13/68; A61F 2013/586–2013/588
USPC ................ 604/385.01, 385.03, 386, 391, 394
See application file for complete search history.

(56) References Cited

U.S. PATENT DOCUMENTS

| | | | |
|---|---|---|---|
| 2001/0014798 A1* | 8/2001 | Fernfors | ........................ 604/390 |
| 2009/0036860 A1 | 2/2009 | Sugiyama et al. | |
| 2011/0125122 A1* | 5/2011 | Thorson et al. | ............ 604/385.3 |

FOREIGN PATENT DOCUMENTS

| | | | |
|---|---|---|---|
| JP | 07-080023 A | 3/1995 | |
| JP | 06-285113 A | 7/2003 | |

(Continued)

OTHER PUBLICATIONS

International Search Report for corresponding International Application No. PCT/JP2011/064666 mailed Sep. 13, 2011.

*Primary Examiner* — Lynne Anderson
*Assistant Examiner* — Kathryn E Ditmer
(74) *Attorney, Agent, or Firm* — Renner, Otto, Boisselle & Sklar, LLP (57) ABSTRACT

Front and back flaps 3F and 3B are protruding past a crotch portion 22 to a same position in the girth direction X; a back member 4b is attached to the back flap 3B, the back member 4b protruding in the girth direction X from an edge of the back flap 3B; a front member 4f protruding in the girth direction X from an edge of the front flap 3F is detachably touch-fastened to a non-skin-contact surface of the front flap 3F which does not contact a skin of the wearer; the crotch portion 22 is folded along a virtual first line L1 parallel to the girth direction X so that a front girth portion 3F and a back girth portion 3B are laid on each other and so that the back member 4b and the front member 4f are facing each other and in contact with each other; and the back member 4b and the front member 4f facing each other are secured to each other in an area where the back member 4b and the front member 4f are in contact with each other.

10 Claims, 11 Drawing Sheets

(56) References Cited

FOREIGN PATENT DOCUMENTS

| | | |
|---|---|---|
| JP | 2005-521475 A | 7/2005 |
| JP | 2005-537039 A | 12/2005 |
| JP | 2006-314771 A | 11/2006 |
| JP | 2007-319177 A | 12/2007 |
| WO | 03/057116 A1 | 7/2003 |
| WO | 03/082167 A2 | 10/2003 |
| WO | 03/082168 A1 | 10/2003 |

* cited by examiner

DISPOSABLE WORN ARTICLE IN PANTS FORM WITH CUT-OUTS AND METHOD FOR MANUFACTURING SAME

This application is a §371 National Stage Application of PCT International Application No. PCT/JP2011/064666 filed Jun. 27, 2011.

TECHNICAL FIELD

The present invention relates to a so-called "reclosable" worn article, i.e., a disposable worn article produced (previously formed) in a pants form, and a method for manufacturing the same.

BACKGROUND ART

In such a reclosable pants-type disposable diaper, a fastening member having a male touch fastener is attached to a back flap, and the male touch fastener is fastened to a front flap.

Such a reclosable diaper can be easily worn by a wearer by himself/herself, and by attaching/detaching the male touch fastener to/from the front flap, it is possible to finely adjust the fit in the girth direction after it is worn and to see if the diaper is dirty after it is worn (see the first patent document).

CITATION LIST

Patent Literature

[First Patent Document] PCT/US2002/039559 (FIG. 1)
[Second Patent Document] JP2006-314771A1 (Abstract)
[Third Patent Document] JP2007-319177A1 (Abstract)

SUMMARY OF INVENTION

Technical Problem

With the conventional structure, however, the fastening member is folded in two during the manufacturing process. The step of folding in two the fastening member, which is a small member, causes an increase in the cost of the product.

Thus, an object of the present invention is to provide a so-called "reclosable worn article", i.e., a disposable worn article produced (previously formed) in a pants form, and a method for manufacturing the same, whereby the product's unit price is low.

Solution to Problem

In order to achieve the object set forth above, a disposable worn article of the present invention is a disposable worn article produced in a pants form, including: a front girth portion extending in a girth direction and covering a front portion of a torso of a wearer; a back girth portion extending in the girth direction and covering a back portion of the torso of the wearer; and a crotch portion being continuous with the front girth portion and the back girth portion, extending in a lengthwise direction perpendicular to the girth direction, and covering a crotch of the wearer, wherein: the front girth portion includes a pair of front flaps protruding past the crotch portion in the girth direction; the back girth portion includes a pair of back flaps protruding past the crotch portion in the girth direction; the front and back flaps are protruding past the crotch portion to a same position in the girth direction; a back member is attached to each of the back flaps, the back member including a protruding portion protruding in the girth direction from an edge of each of the back flaps in the girth direction; a front member including a protruding portion protruding in the girth direction from an edge of each of the front flaps in the girth direction is detachably touch-fastened to a non-skin-contact surface of each of the front flaps which is contactless to a skin of the wearer; the crotch portion is folded along a virtual first line parallel to the girth direction so that the front girth portion and the back girth portion are laid on each other and so that the protruding portions of the back member and the front member are facing each other and in contact with each other; and the protruding portions of the back member and the front member facing each other are secured to each other.

Such a worn article is manufactured through the following steps, for example.

That is, a method for manufacturing a worn article of the present invention includes a carrying step of carrying one or two webs to be the front and back flaps in a plurality of worn articles; a placement step of placing absorbent main bodies, each of which forms a part or whole of the crotch portion, one after another on the web, thereby forming a continuous laminate; a boring step of forming back holes in portions of the web which are to be the back flaps adjacent to each other; a boring step of forming front holes in portions of the web which are to be the front flaps adjacent to each other; an attachment step of placing first members on the web so that each of the first members extends over each of the back holes in the girth direction and each of the first members is to provide two of the back members, and attaching opposite end portions of each of the first members to the web in a vicinity of each of the back holes; a fastening step of placing second members on the web so that each of the second members extends over each of the front holes in the girth direction and each of the second members is to provide two of the front members, and detachably touch-fastening opposite end portions of each of the second members to the web in a vicinity of each of the front holes; a folding step of folding each of the absorbent main bodies along the first line so that the back holes and the front holes are aligned with each other and so that a portion of each of the first members and a portion of each of the second members are facing each other and in contact with each other through the two holes aligned together; a securing step of securing together the portion of each of the first members and the portion of each of the second members, which are facing each other and in contact with each other through the two holes aligned together; and a severing step of cutting the web, the first members and the second members along a line passing through an area of the holes aligned together, thereby severing and producing individual worn articles off the continuous laminate.

Advantageous Effects of Invention

According to the present invention, the back member and the front member are in contact with each other and are secured to each other through the cut-outs (holes). Therefore, the conventional step of folding the fastening member in two is no longer needed. As a result, it will be easier to manufacture reclosable worn articles, and it will be possible to reduce the cost.

BRIEF DESCRIPTION OF DRAWINGS

FIGS. 1A to 1C illustrate an embodiment of a worn article formed in a pants shape of the present invention, wherein

FIG. 10 is a plan view showing another example of the worn article unfolded.

DESCRIPTION OF EMBODIMENTS

In a preferred embodiment of the present invention, each of the front and back flaps includes a cut-out receding (indented) in the girth direction from the edge of each of the flaps in the girth direction; in the cut-out of each of the back flaps, the back member protrudes in the girth direction from the edge of each of the back flaps; in the cut-out of each of the front flaps, the front member protrudes in the girth direction from the edge of each of the front flaps; and the protruding portions of the front member and the back member, which are protruding in the cut-out, are secured to each other.

In this case, the front flap and the back flap can be secured to each other through the cut-out during the manufacturing process.

In a preferred embodiment of the present invention, each of the cut-outs is formed at a center apart from upper and lower ends of the corresponding flap in the lengthwise direction, whereby each of the front and back flaps is hollowed at the edge thereof.

In this case, the fastening member composed of the front member and the back member is continuous in an area of the flaps at the center thereof in the up-down direction. Therefore, the force by which the front flap and the back flap are coupled to each other in the girth direction is likely to act upon the front and back girth portions, whereby it is unlikely to "come loose".

In a more preferred embodiment of the present invention, the protruding portions of the back member and the front member are secured to each other by being welded to each other.

In this case, the front member and the back member can be easily integrated together.

In a more preferred embodiment of the present invention, the back member is secured to each of the back flaps, and the front member includes a male touch fastener detachably touch-fastened to each of the front flaps.

In a more preferred embodiment of the present invention, a line of the edge of each of the front flaps and a line of the edge of each of the back flaps are aligned with each other in the girth direction; and a line defining an end of the front member in the girth direction and a line defining an end of the back member in the girth direction are aligned with each other.

Thus, where the lines of the edges or ends are aligned flush with each other, the flaps, the front member and the back member can be cut together while being laid on each other during the manufacturing process.

Another manufacturing method of the present invention comprises: a carrying step of carrying one or two webs to be the front and back flaps in a plurality of worn articles; a placement step of placing absorbent main bodies, each of which forms a part or whole of the crotch portion, one after another on the web, thereby forming a continuous laminate; a folding step of folding the absorbent main bodies along the first line so that the front and back flaps are laid on each other; a boring step of forming a back hole and a front hole aligned with each other in portions to be each of the front flaps and each of the back flaps laid on each other after the folding step; an attachment step of placing first members on the web so that each of the first members extends over each of the back holes in the girth direction and each of the first members is to provide two of the back members, and attaching opposite end portions of each of the first members to the web in a vicinity of each of the back holes; a fastening step of placing second members on the web so that each of the second members extends over each of the front holes in the girth direction and each of the second members is to provide two of the front members, and detachably touch-fastening opposite end portions of each of the second members to the web in a vicinity of each of the front holes; a securing step of securing together the first members and the second members in an area where the first members and the second members are facing each other and in contact with each other through the front holes and the back holes aligned together; and a severing step of cutting the web, the first members and the second members along a line passing through an area of the holes aligned together, thereby severing and producing individual worn articles off the continuous laminate.

In this case, the continuous laminate is folded in two, and the front and back holes can be formed at once while portions of the web to be the front flap and the back flap are laid on each other. Therefore, the shapes and the positions of the two holes coincide with each other. Thus, the size of the holes can be made as small as possible.

[Embodiments]

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

Embodiment 1 of the present invention will now be described with reference to the drawings.

FIGS. 1A to 7 show Embodiment 1.

Figure 1A:
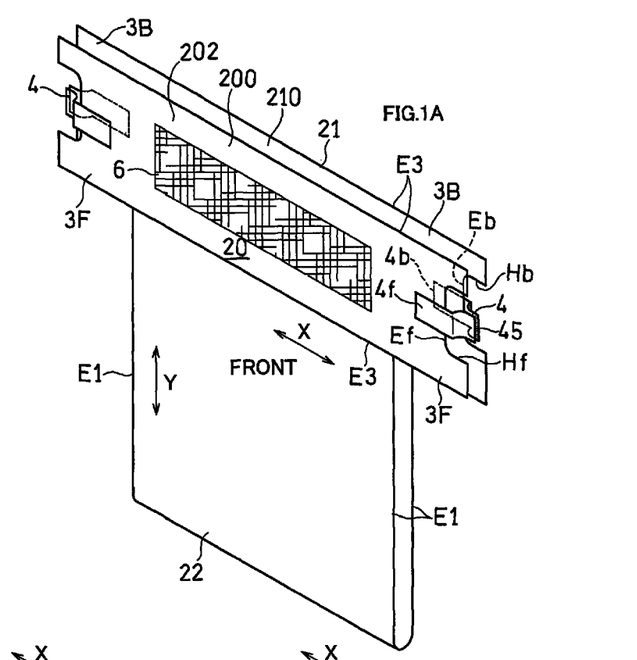
FIG. 1A is a schematic perspective view showing the worn article as seen from a diagonal front direction.
Figure 4A:
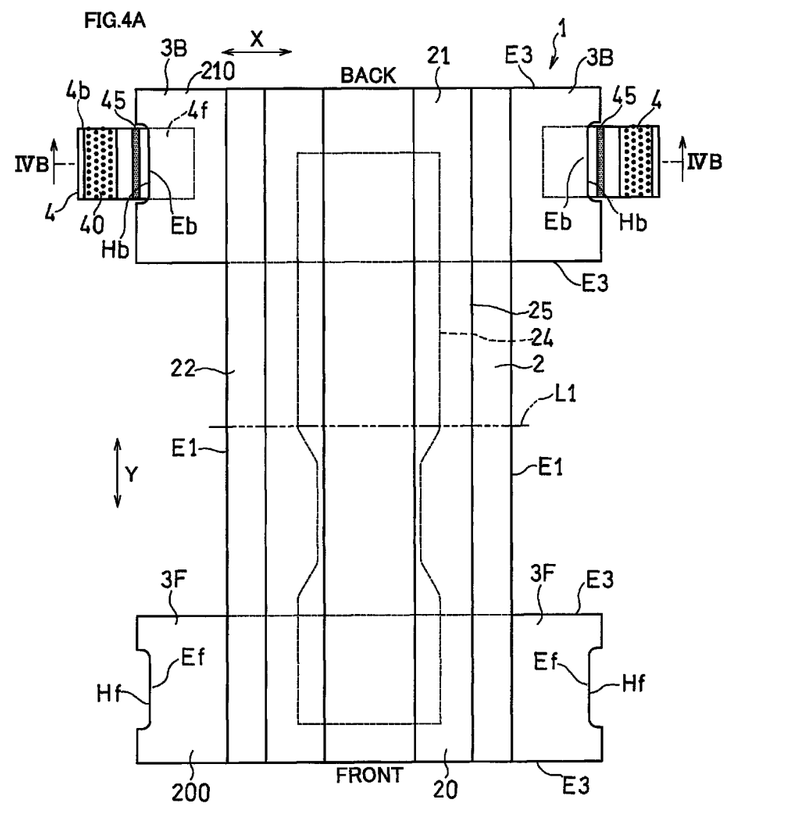
FIG. 4A is a front view showing the worn article unfolded.

Worn Article 1:

As shown in FIGS. 1A and 4A, a worn article 1 of the present embodiment 1 includes an absorbent main body (diaper main body) 2, a front flap (a portion of the front girth portion) 3F, and a back flap (a portion of the back girth portion) 3B. The absorbent main body 2 includes a front portion (the front girth portion) 20 extending in the girth direction X covering the front torso of the wearer, a back portion (the back girth portion) 21 extending in the girth direction X covering the back torso of the wearer, and a crotch portion 22 covering the crotch between the front portion 20 and the back portion 21.

The crotch portion 22 is continuous with the front portion 20 and the back portion 21, and extends in the vertical (lengthwise) direction Y perpendicular to the girth direction X. The absorbent main body 2 form a part or whole of the crotch portion 22.

Figure 3A:
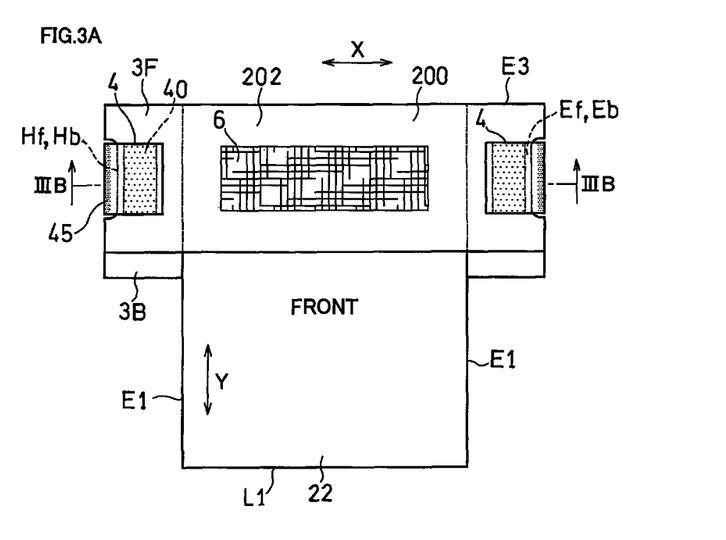
FIG. 3A is a front view showing the pants-shaped worn article.

As shown in FIG. 3A, the crotch portion 22 is folded in two along the virtual first line L1 parallel to the girth direction X. Thus, the front flap 3F and the back flap 3B are laid on each other. In FIG. 4A, a front girth member 200 forming the front flap 3F is stuck onto one end portion of the front portion 20 of the absorbent main body 2 in the vertical (lengthwise) direction Y. On the other hand, a back girth member 210 forming the back flap 3B is stuck onto the other end portion of the back portion 21 of the absorbent main body 2 in the vertical (lengthwise) direction Y.

The front and back girth members 200 and 210 are protruding from the absorbent main body 2 in the girth direction X and are forming parts of the front and back girth portions.

Figure 1B:
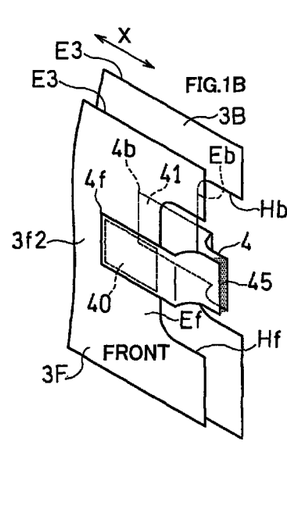
FIG. 1B is a perspective view showing a fastened portion.

As shown in FIG. 1A, the flaps 3F and 3B are protruding past the crotch portion 22 in the girth direction X, and are extending in the girth direction X from opposite edges E1 of the absorbent main body 2 (the crotch portion 22). As shown in FIG. 1B, a fastening member 4 having a male touch fastener (fastening surface) 40 is secured to each of the pair of back flaps 3B.

Note that the first fastening member may be a tape material with an adhesive applied thereon, instead of the male touch fastener 40, and in such a case, a surface to which the adhesive is likely to adhere needs to be provided on the front flap 3F, etc.

In the present embodiment, a non-skin-contact surface 202 of the front girth member 200 of FIG. 1A is formed by a non-woven fabric. In this case, the male touch fastener 40 engages with the non-woven fabric. Note that a second fastening member 6 made of a female touch fastener may be provided on the non-skin-contact surface 202 of the front portion 20.

The term "skin-contact surface side" as used herein refers to the side which faces the skin surface of the wearer when the worn article 1 is worn, and the term "non-skin-contact surface side" refers to the side opposite to the skin-contact surface side.

Figure 2A:
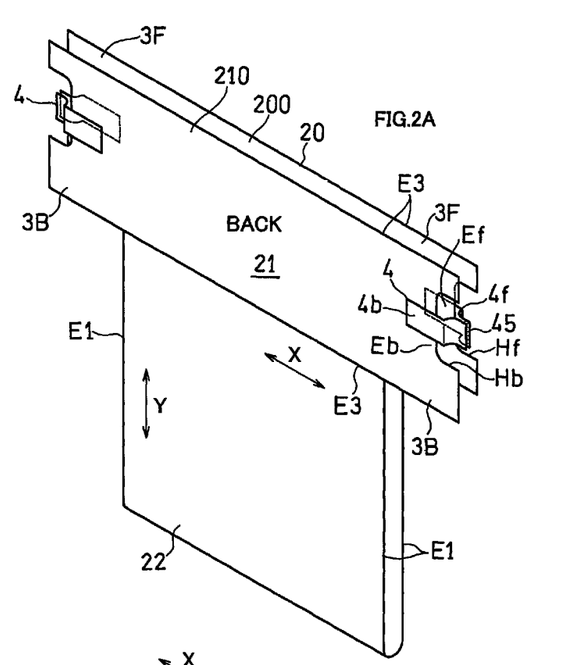
FIG. 2A is a schematic perspective view showing the pants-shaped worn article as seen from a diagonal rear direction.

As shown in FIGS. 1A and 2A, when the article is worn, the fastening member 4 includes a protruding portion 45 extending in the girth direction X from the edges Ef and Eb of the flaps 3F and 3B in the girth direction X, in cut-outs Hf and Hb of the front flap 3F and the back flap 3B. As shown in FIG. 1B, the fastening member 4 includes the male touch fastener 40 touch-fastened to a non-skin-contact surface 3f2 of the front flap 3F when worn, and a secured portion 41 secured to the back flap 3B.

Figure 1C:
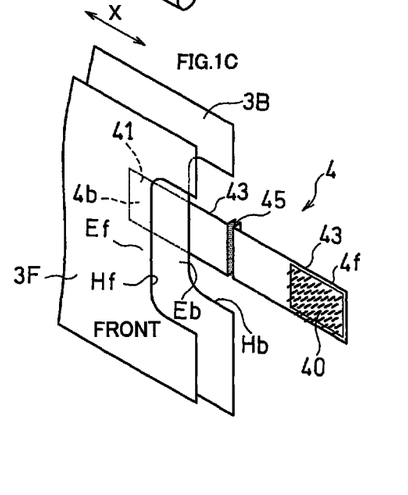

In FIG. 1C, the fastening member 4 includes a base material 43 made of a resin, and a fastener material, which forms the male touch fastener 40, stuck onto a portion of the base material 43. As shown in FIG. 1C, with the male touch fastener 40 detached from the front flap 3F, the portion of the male touch fastener 40 is protruding from the back flap 3B in the girth direction X.

An absorbent core 24 shown by a broken line is provided on the absorbent main body 2 of FIG. 4A, and the absorbent main body 2 absorbs body fluid. Standing gathers 25 may be provided on the absorbent main body 2.

The absorbent main body 2 may include around-leg portions which are hollowed in conformity with the legs of the wearer. Elastic members formed by rubber threads, or the like, for example, may be provided so as to conform to the legs of the wearer in the around-leg portions or portions of the flaps 3 that are connected to the around-leg portions.

Moreover, an elastic member for fitting the worn article 1 to the wearer may be provided in portions of the front portion 20 and the back portion 21 of the absorbent main body 2 which are to be present around the torso and in the front and back flaps 3F and 3B. The elastic member may be, for example, a plurality of rubber threads or rubber tapes, a film, or a material including a thermoplastic resin, or the like.

Next, the configuration (structure) of the present diaper when worn will be described.

As shown in FIG. 1A, when worn, the absorbent main body 2 is folded in two in the crotch portion 22, and the skin-contact surface of the front portion 20 and the skin-contact surface of the back portion 21 are facing each other with the wearer therebetween.

The worn article 1 can be worn by the wearer himself/herself in the state of FIG. 1A, and it is possible to change the waist size of the worn article 1 in accordance with the size of the torso of the wearer, after it is worn, by detaching the male touch fastener 40 of FIG. 1C from the front flap 3F and the touch-fastening the male touch fastener 40 onto the front flap 3F or the front portion 20 again as shown in FIG. 1B.

In this process, the front flap 3F is stretched in the girth direction X from the front portion toward the back portion of the torso, whereas the back flap 3B is stretched in the girth direction X from the back portion toward the front portion. The back flap 3B is laid partially over the front flap 3F in the side portion or the front portion of the torso of the wearer.

Next, an important part of the present invention will be described.

In FIGS. 1A and 2A, the front and back flaps 3F and 3B are protruding past the crotch portion 22 to the same position in the girth direction X.

The front and back flaps 3F and 3B include the cut-outs Hf and Hb receding (indented) in the girth direction X from the edges Ef and Eb of the flaps 3F and 3B. In the present embodiment, as shown in FIG. 1C, the cut-outs Hf and Hb are formed at the center apart from the upper and lower ends E3 (FIG. 1A) of the flaps 3F and 3B in the vertical direction Y. Therefore, the flaps 3F and 3B are hollowed at the edges Ef and Eb.

At the edges Ef and Eb of the flaps 3F and 3B, the cut-out Hf of the front flap 3F and the cut-out Hb of the back flap 3B are laid at least partially on each other.

The fastening member 4 is formed by a front member 4f and a back member 4b. With the crotch portion 22 folded in two along the first line L1 as shown in FIG. 3A, the front member 4f and the back member 4b of FIG. 1B are facing each other and in contact with each other through the cut-outs Hf and Hb.

The front member 4f and the back member 4b are welded and coupled together in the protruding portion 45, where they are facing each other and in contact with each other, and on the skin-contact surface. The protruding portion 45 is formed in the first end portion of the front member 4f and the back member 4b in the girth direction X.

The back member 4b is secured to the back flap 3B in the second end portion which is on the opposite side from the protruding portion 45 in the girth direction X. In the cut-out Hb, the first end portion of the back member 4b (the protruding portion 45) is protruding in the girth direction X from the edge Eb of the back flap 3B.

Figure 2B:
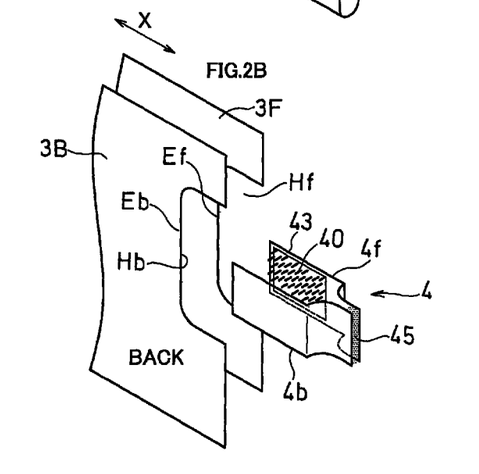
FIG. 2B is an exploded perspective view showing the fastened portion with the fastening members separated from the front and back flaps.

As explicitly shown in FIGS. 1C and 2B, the male touch fastener 40 is secured to the front member 4f. The portion of the front member 4f where the male touch fastener 40 is provided is touch-fastened to the non-skin-contact surface 3f2 (FIG. 1B) at the edge of the front flap 3F. In the cut-out Hf, the first end portion of the front member 4f (the protruding portion 45) of FIG. 1B is protruding in the girth direction X from the edge Ef of the front flap 3F.

In the girth direction X of FIG. 1B, the line of the edge of the front flap 3F and the line of the edge of the back flap 3B are aligned with each other. Moreover, the line of an end of the front member 4f on the side of the first end portion and the line of an end of the back member 4b on the side of the first end portion are aligned with each other.

Note that the proportion in terms of shape and size between the cut-outs Hb and Hf, the front member 4f, and the back member 4b is preferably as shown in FIGS. 3A and 4A. However, in FIGS. 1A to 2B, the cut-outs Hb and Hf are shown to be larger and the front member 4f and the back member 4b are shown to have a smaller vertical width for the sake of easy understanding of the structure of the cut-outs Hb and Hf, the front member 4f and the back member 4b.

In FIGS. 1A, 1B, 2A and 2B, in order to better illustrate the front member 4f and the back member 4b, these members are shown to be folded (bent), but these members 4f and 4b are actually in an unfolded flat shape, as shown in FIG. 1C, or a shape conforming in the girth direction.

Figure 3B:
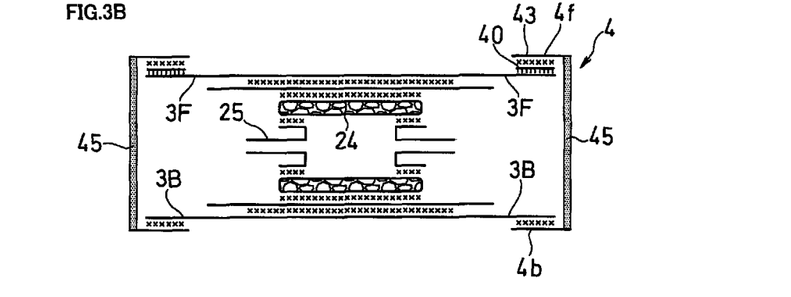
FIG. 3B is a conceptual cross-sectional view taken along line IIIB-IIIB showing the worn article.
Figure 4B:
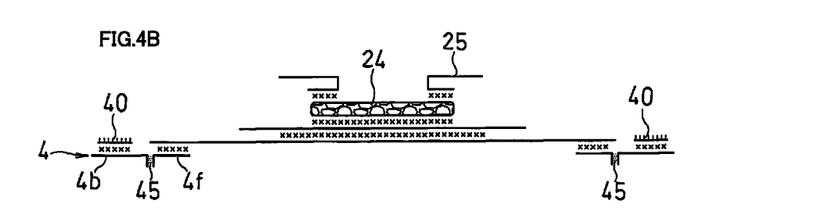
FIG. 4B is a conceptual cross-sectional view taken along line IVB-IVB showing the worn article.
Figure 5:
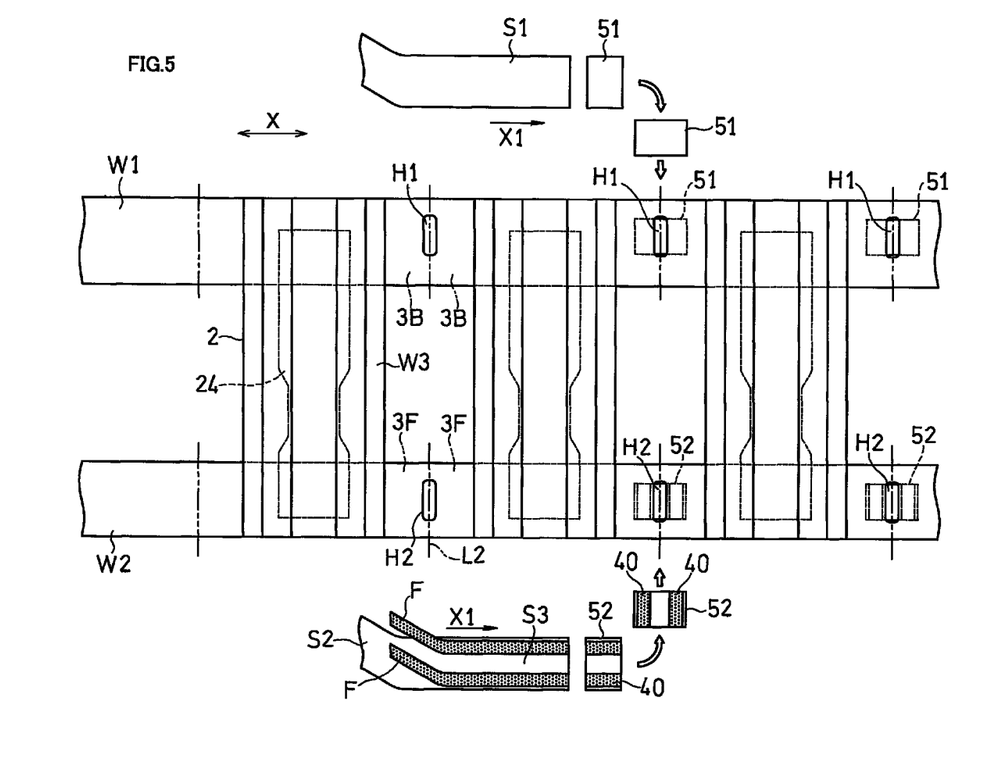
FIG. 5 is a plan view showing a manufacturing step of the worn article.

In FIGS. 1A to 4B, the secured portion of the protruding portion 45 is dotted, wherein other bonded portions or secured portions are denoted by multiple x's as shown in FIGS. 3B and 4B, and the male touch fasteners 40 of FIGS. 4A and 5 are dotted with larger dots.

Next, an example of a method for manufacturing the present worn article 1 will be described with reference to FIGS. 5 to 7.

While first and second continuous webs W1 and W2 to be girth portions including flaps are carried in the longitudinal direction X1, the absorbent main bodies 2 are provided on, and secured to, the two webs W1 and W2 so as to bridge the gap therebetween. Thus, a continuous laminate W3 to be a larger number of worn articles 1 is produced.

After the production of the continuous laminate W3, a back hole H1 accounting for two cut-outs Hb (FIG. 1A) is formed by die-cut in a portion of the first continuous web W1 to be adjacent back flaps 3B, while a front hole H2 accounting for two cut-outs Hf (FIG. 1A) is formed by die-cut in a portion of the second continuous web W2 to be adjacent front flaps 3F. The holes H1 and H2 are formed along the second line L2 so that their shape and position are in line symmetry with respect to the virtual second line L2, which is used for severing the continuous laminate W3 into individual worn articles 1.

On the other hand, a first member 51 forming the back member 4b (FIG. 2B) and a second member 52 forming the front member 4f (FIG. 1B) are produced as follows.

In FIG. 5, while a first continuous sheet S1 of the same material as the base material 43 is carried in the longitudinal direction X1, the first continuous sheet S1 is cut off successively at the tip thereof, producing the first members 51. The first member 51 is to be two of the back members 4b (FIG. 2B).

On the other hand, while a second continuous sheet S2 to be the base material 43 is carried in the longitudinal direction X1, a pair of continuous fastener materials F to be the male touch fasteners 40 is welded and stuck onto the second continuous sheet S2. Thus, a continuous member S3 to be the front member 4f is produced.

The continuous member S3 is successively cut off at the tip thereof, producing the second members 52. The second member 52 is to be two of the front members 4f (FIG. 1B).

As shown in FIG. 5, the first and second members 51 and 52 are rotated by 90° with respect to the longitudinal direction X1 before they are placed on the first and second continuous webs W1 and W2, respectively.

After forming the holes H1 and H2, the first members 51 are placed on the first continuous web W1 so that each first member 51 extends over the back hole H1 in the girth direction X, and the opposite end portions of the first member 51 are secured to the first continuous web W1 by welding or bonding in the vicinity of the back hole H1. The opposite end portions of the first member 51 correspond to the secured portion 41 of FIG. 1B.

On the other hand, the second members 52 are placed on the second continuous web W2 so that each second member 52 extends over the front hole H2 in the girth direction X, and the opposite end portions of the second member 52 are detachably touch-fastened to the second continuous web W2 by means of the male touch fastener 40 in the vicinity of the front hole H2.

Figure 6:
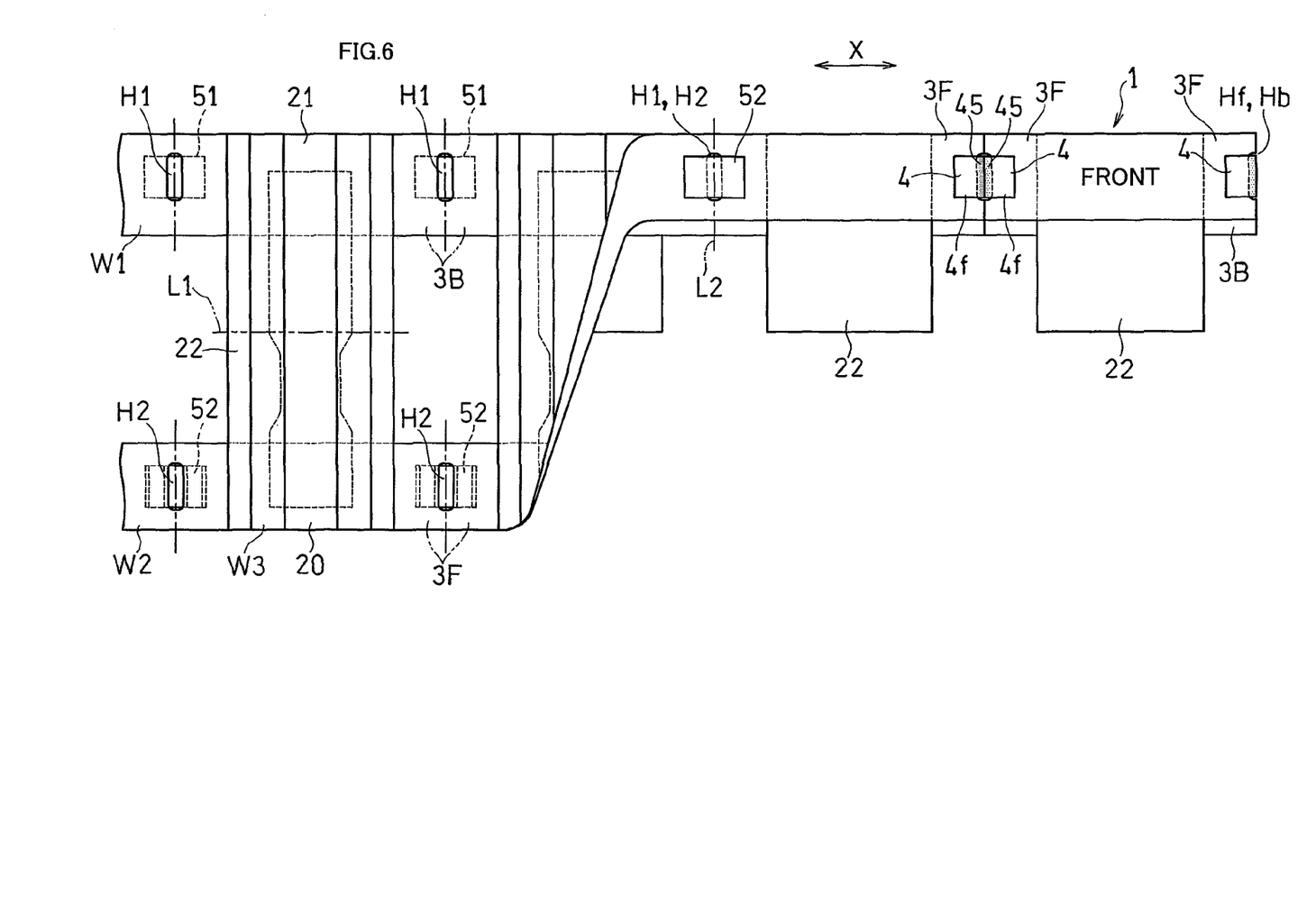
FIG. 6 is a plan view showing a manufacturing step of the worn article.

Thereafter, the continuous laminate W3 of FIG. 6 is folded in two in the crotch portion 22 along the virtual first line L1 parallel to the girth direction X so that the first continuous web W1 and the second continuous web W2 are laid on each other, i.e., so that the front portion 20 and the back portion 21 are laid on each other. In this folding step, as shown in FIG. 7, the absorbent main body 2 is folded in two along the first line L1 of FIG. 6 so that the back hole H1 and the front hole 112 are aligned with each other and so that the first member 51 and the second member 52 are facing each other and in contact with each other through the holes H1 and H2 aligned together.

Figure 7:
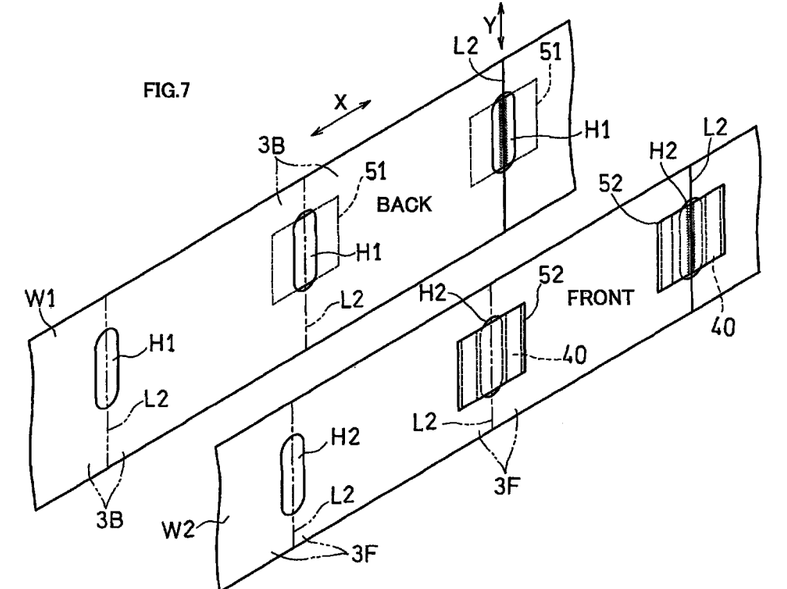
FIG. 7 is a perspective view showing the first web and the second web separated from each other, showing a method for fastening the front member (first member) and the back member (second member) together in the manufacturing step.

Next, as shown in FIGS. 6 and 7, the first member 51 and the second member 52 are welded and secured together in an area where the first member 51 and the second member 52 are facing each other and in contact with each other through the holes H1 and H2 aligned together. During or after this securing process, the webs W1 and W2, the first member 51 and the second member 52 are cut along the virtual second line L2 extending in the vertical direction Y (the line passing through the area of the holes H1 and H2) at a position including the holes H1 and H2 aligned together, thereby severing the continuous laminate W3 of FIG. 6 into individual worn articles 1.

The reclosable pants-type diaper (the worn article 1) shown in FIG. 1A is produced as described above.

Now, by welding together the two members of the fastening member 4 of FIG. 1B, i.e., the front member 4f and the back member 4b, in the protruding portion 45, it is possible to obtain a form similar to the fastening member 4 folded in two, thus eliminating the need to fold in two the fastening member 4, which is a small part. This facilitates the production of the reclosable-type worn article 1.

Note that one end of the cut-off line, along which the webs W1 and W2 are cut, crosses the periphery of the holes H1 and 112, and the other end thereof crosses the edge of the webs W1 and W2. That is, the cut-off line, along which the webs W1 and W2 are cut, extends from the periphery of the holes H1 and H2 to the edge of the webs W1 and W2.

Next, another method for manufacturing the present worn article 1 will be described with reference to FIGS. 8 and 9.

In this example, the boring step for boring the holes H1 and H2 and the placement step for placing the first and second members 51 and 52 are performed, after the continuous laminate W3 is folded in two along the first line L1.

Figure 8:
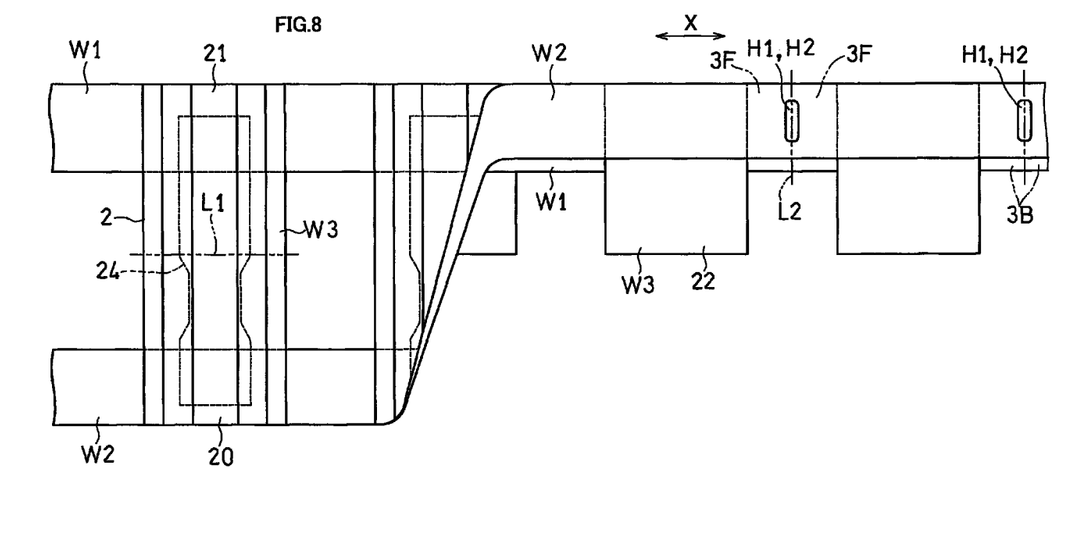
FIG. 8 is a plan view showing another example of the manufacturing method.

In FIG. 8, while the first and second continuous webs W1 and W2 are carried in the longitudinal direction X1, the absorbent main bodies 2 are provided on, and secured to, the two webs W1 and W2 so as to bridge the gap therebetween. Thus, the continuous laminate W3 to be the worn articles 1 is produced.

The absorbent main body 2 is folded along the first line L1 so that the front and back flaps 3F and 3B are laid on each other. After the folding step, the back hole H1 and the front hole 112 are formed at the same time through a single die-cut operation in portions to be the front flap 3F and the back flap 3B laid on each other.

If the two holes H1 and 2 are punched at the same time after the absorbent main body 2 is folded so that the front flap 3F and the back flap 3B are laid on each other, as described above, the holes H1 and H2 will have a completely matching shape and position. Thus, it is possible to reduce the size of the holes H1 and H2.

Figure 9:
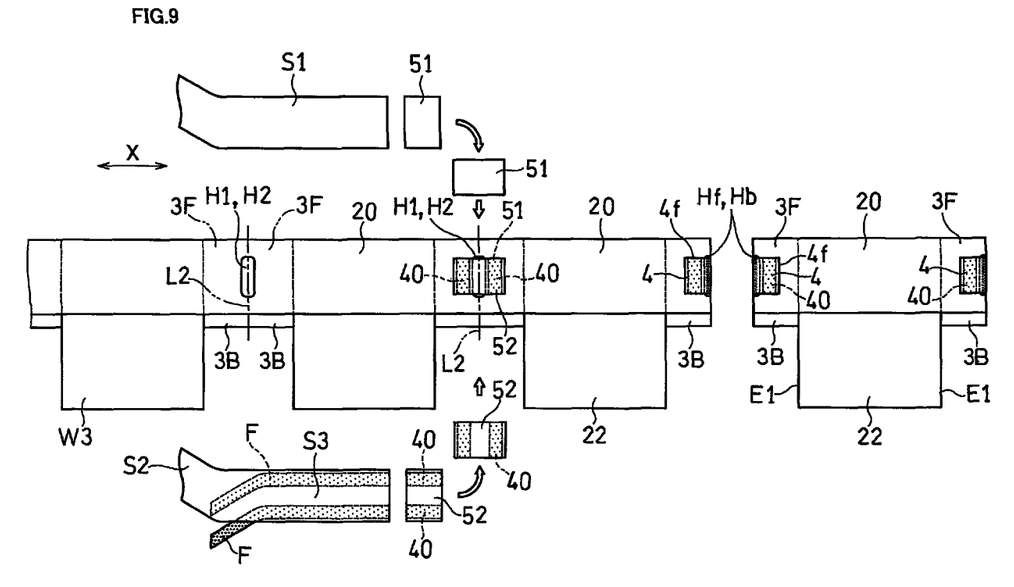
FIG. 9 is a plan view showing another example of the manufacturing method.

As shown in FIG. 9, after forming the holes H1 and H2, the first members 51 are placed on the first continuous web W1 so that each first member 51 extends over the back hole H1 in the girth direction X, and opposite end portions of the first member 51 are bonded and secured to the first continuous web W1 using a hot-melt resin, or the like, in the vicinity of the back hole H1.

The method for producing the first member is similar to Embodiment 1, and will not be described below.

On the other hand, the second members 52 are placed on the second continuous web W2 so that each second member 52 extends over the front hole H2 in the girth direction X, and the opposite end portions of the second member 52 are detachably touch-fastened to the second continuous web W2 by means of the male touch fastener 40 in the vicinity of the front hole 112.

In this manufacturing method, the second members 52 are produced by successively cutting off the tip of the continuous member S3, which includes the second continuous sheet S2 welded and stuck onto a pair of continuous fastener materials F.

As shown in FIG. 9, as in Embodiment 1, the first and second members 51 and 52 are rotated by 90° with respect to the longitudinal direction X1 before they are placed on the first and second continuous webs W1 and W2, respectively.

Next, a portion of the first member 51 and a portion of the second member 52 are welded and secured together in an area where the first member 51 and the second member 52 are facing each other and in contact with each other through the holes H1 and H2 aligned together. During or after this securing process, the webs W1 and W2, the first member 51 and the second member 52 are cut along the virtual second line L2 extending in the vertical direction Y (the line passing through the area of the holes 111 and 112) at a position including the holes H1 and H2 aligned together, thereby severing the continuous laminate W3 into the individual worn articles 1 of FIG. 6.

The reclosable pants-type diaper (the worn article 1) shown in FIG. 1A is produced as described above.

Figure 10:
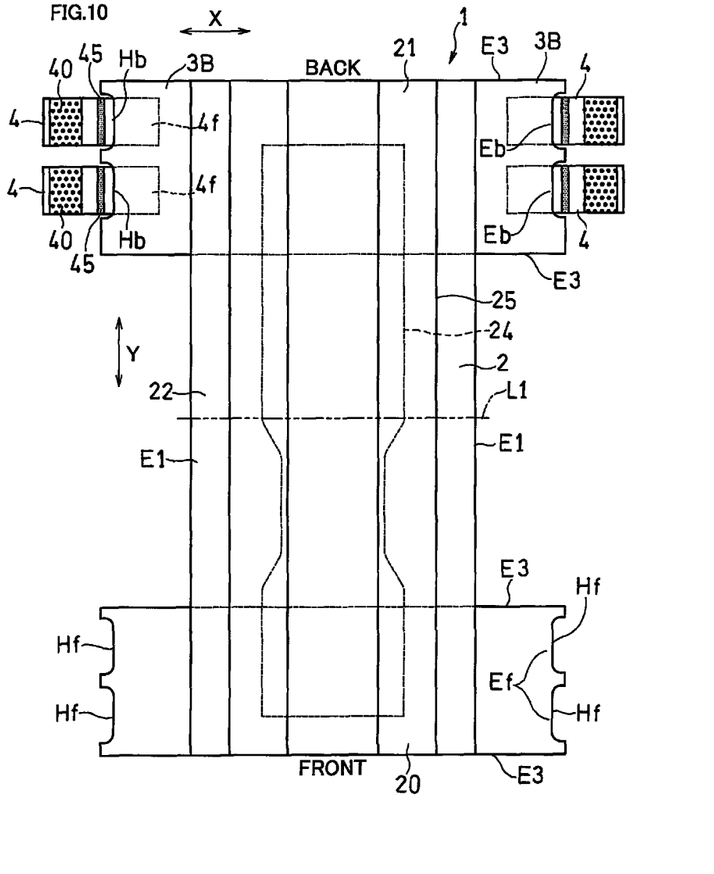
FIG. 10 is a perspective view showing the fastened portion with the male touch fastener detached from the front flap.

FIG. 10 shows another example of the worn article 1.

As shown in FIG. 10, two cut-outs Hb and Hb may be provided in each back flap 3B, with the fastening member 4 provided for each of the cut-outs Hb and Hb.

Figure 11A:
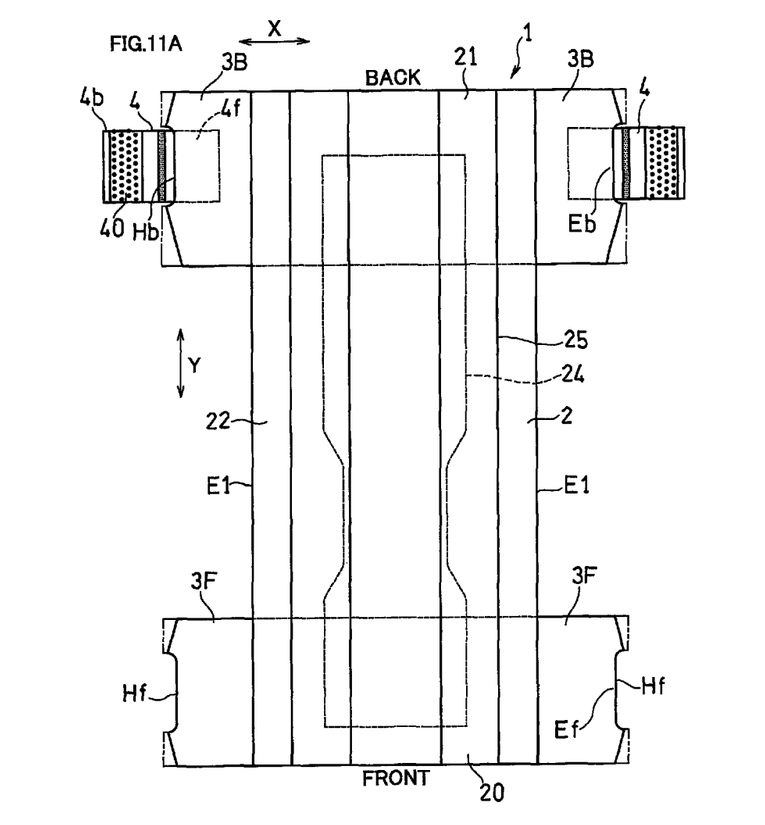
FIG. 11A is a plan view showing still another example of the worn article unfolded.

FIG. 11A shows still another example of the worn article 1.

Figure 11B:
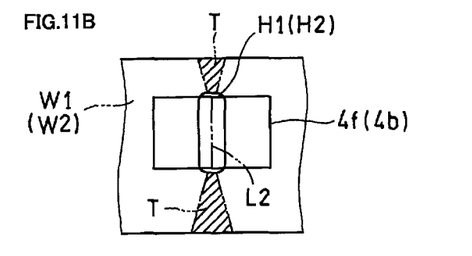
FIG. 11B is a plan view showing the severing step during the manufacturing process of the worn article.

In this example, when cutting the first and second continuous webs W1 and W2 during the severing step of FIG. 11B, hatched portions T are trimmed off, whereby it is possible to remove the protruding portions above and below the fastening member 4 of FIG. 11A.

INDUSTRIAL APPLICABILITY

The present invention is applicable to a disposable worn article produced in a pants form, and a method for manufacturing the same.

REFERENCE SIGNS LIST

1: Worn article
2: Absorbent main body
4: Fastening member
4f: Front member
4b: Back member
20: Front portion
21: Back portion
22: Crotch portion
40: Male touch fastener
41: Secured portion
43: Base material
45: Protruding portion
51: First member
52: Second member
200: Front girth member
210: Back girth member
3B: Back flap
3F: Front flap
E1: Edge of main body
Eb: End portion
Ef End portion
E3: Upper and lower edges
Hb: Cut-out
Hf: Cut-out
X: Girth direction
Y: Vertical direction

The invention claimed is:

1. A disposable worn article produced in a pants form, including:
   a front girth portion extending in a girth direction and adapted to cover a front portion of a torso of a wearer,
   a back girth portion extending in the girth direction and adapted to cover a back portion of the torso of the wearer, and
   a crotch portion being continuous with the front girth portion and the back girth portion, extending in a lengthwise direction perpendicular to the girth direction, and adapted to cover a crotch of the wearer, wherein:
   the front girth portion includes a pair of front flaps protruding past the crotch portion in the girth direction,
   the back girth portion includes a pair of back flaps protruding past the crotch portion in the girth direction,
   a fastening member is secured to each of the pair of back flaps,
   by attaching and detaching the fastening member to and from each of the front flaps, it is possible to finely adjust a fit in the girth direction after the worn article is worn and to see if the worn article is dirty after the worn article is worn, and
   the front and back flaps protrude past the crotch portion to a same position in the girth direction;
   the worn article further including:

a back member of the fastening member attached to each of the back flaps, the back member including a protruding portion protruding in the girth direction from an edge of each of the back flaps in the girth direction;

a front member of the fastening member including a protruding porting protruding in the girth direction from an edge of each of the front flaps in the girth direction being detachably touch-fastened to a non-skin-contact surface of each of the front flaps which is contactless to a skin of the wearer;

the crotch portion folded along a virtual first line parallel to the girth direction so that the front girth portion and the back girth portion are laid on each other and so that the protruding portions of the back member and the front member are facing each other and in contact with each other;

the protruding portions of the back member and the front member facing each other being secured to each other;

wherein, subsequent to manufacture and prior to use of the worn article, the edges in the girth direction of the front and back flaps are not directly secured to each other but rather are attached to each other only via the respective front and back members that are secured to each other; and wherein:

each of the front and back flaps includes a cut-out receding in the girth direction from the edge of each of the flaps in the girth direction;

in the cut-out of each of the back flaps, the back member protrudes in the girth direction from the edge of each of the back flaps;

in the cut-out of each of the front flaps, the front member protrudes in the girth direction from the edge of each of the front flaps; and the protruding portions of the front member and the back member, which are protruding in each of the cut-outs, are secured to each other.

2. A worn article according to claim 1, wherein each of the cut-outs is formed at a center apart from upper and lower ends of the corresponding flap in the lengthwise direction, whereby each of the front and back flaps is hollowed at the edge thereof.

3. A worn article according to claim 2, wherein the protruding portions of the back member and the front member are secured to each other by being welded to each other.

4. A worn article according to claim 3, wherein the back member is secured to each of the back flaps, and the front member includes a male touch fastener detachably touch-fastened to each of the front flaps.

5. A worn article according to claim 4, wherein:

a line of the edge of each of the front flaps and a line of the edge of each of the back flaps are aligned with each other in the girth direction; and a line defining an end of the front member in the girth direction and a line defining an end of the back member in the girth direction are aligned with each other.

6. A method for manufacturing a disposable worn article according to claim 1, the method comprising:

a carrying step of carrying one or two webs to be the front and back flaps in a plurality of worn articles;

a placement step of placing absorbent main bodies, each of which forms a part or whole of the crotch portion, one after another on the web, thereby forming a continuous laminate;

a boring step of forming back holes in portions of the web which are to be the back flaps adjacent to each other;

a boring step of forming front holes in portions of the web which are to be the front flaps adjacent to each other;

an attachment step of placing first members on the web so that each of the first members extends over each of the back holes in the girth direction and each of the first members is to provide two of the back members, and attaching opposite end portions of each of the first members to the web in a vicinity of each of the back holes;

a fastening step of placing second members on the web so that each of the second members extends over each of the front holes in the girth direction and each of the second members is to provide two of the front members, and detachably touch-fastening opposite end portions of each of the second members to the web in a vicinity of each of the front holes;

a folding step of folding each of the absorbent main bodies along the first line so that the back holes and the front holes are aligned with each other and so that a portion of each of the first members and a portion of each of the second members are facing each other and in contact with each other through the two holes aligned together;

a securing step of securing together the portion of each of the first members and the portion of each of the second members, which are facing each other and in contact with each other through the two holes aligned together; and a severing step of cutting the web, the first members and the second members along a line passing through an area of the holes aligned together, thereby severing and producing individual worn articles off the continuous laminate.

7. A method according to claim 6, wherein in the severing step, the line passing through the area of the holes is a virtual second line extending in the lengthwise direction, and the web, the first members and the second members are cut along the second line.

8. A method according to claim 7, wherein:

the two webs comprise a first continuous web to be the back flaps and a second continuous web to be the front flaps; and the absorbent main bodies are placed so as to bridge between the first continuous web and the second continuous web.

9. A method for manufacturing a disposable worn article according to claim 1, the method comprising:

a carrying step of carrying one or two webs to be the front and back flaps in a plurality of worn articles;

a placement step of placing absorbent main bodies, each of which forms a part or whole of the crotch portion, one after another on the web, thereby forming a continuous laminate;

a folding step of folding the absorbent main bodies along the first line so that the front and back flaps are laid on each other;

a boring step of forming a back hole and a front hole aligned with each other in portions to be each of the front flaps and each of the back flaps laid on each other after the folding step;

an attachment step of placing first members on the web so that each of the first members extends over each of the back holes in the girth direction and each of the first members is to provide two of the back members, and attaching opposite end portions of each of the first members to the web in a vicinity of each of the back holes;

a fastening step of placing second members on the web so that each of the second members extends over each of the front holes in the girth direction and each of the second members is to provide two of the front members, and detachably touch-fastening opposite end portions of each of the second members to the web in a vicinity of each of the front holes;

a securing step of securing together the first members and the second members in an area where the first members and the second members are facing each other and in contact with each other through the front holes and the back holes aligned together; and a severing step of cutting the web, the first members and the second members along a line passing through an area of the holes aligned together, thereby severing and producing individual worn articles off the continuous laminate.

10. A method according to claim 9, wherein:

the two webs comprise a first continuous web to be the back flaps and a second continuous web to be the front flaps; and the absorbent main bodies are placed so as to bridge between the first continuous web and the second continuous web.

\* \* \* \* \*